US00PP10234P

United States Patent [19]

Adolph

[11] Patent Number: Plant 10,234

[45] Date of Patent: Feb. 10, 1998

[54] PETUNIA PLANT NAMED MICHEL

[75] Inventor: Ernest Adolph, Scharrachbergheim, France

[73] Assignee: Plantagen S.A., Scharrachbergheim, France

[21] Appl. No.: 715,553

[22] Filed: Sep. 19, 1996

[51] Int. Cl.[6] ..... A01H 5/00

[52] U.S. Cl. ..... Plt./68.1

[58] Field of Search ..... Plt./68.1

*Primary Examiner*—James R. Feyrer
*Assistant Examiner*—Melissa L. Kimball
*Attorney, Agent, or Firm*—C. A. Whealy

[57] ABSTRACT

A distinct cultivar of Petunia plant named 'Michel', characterized by its bright red flowers; floriferous with numerous flowers per plant; early flowering; vigorous growth habit and moderate growth rate; spreading plant habit and freely branching; strong, healthy foliage; and moderate tolerance to rain, drought and temperature extremes.

2 Drawing Sheets

The present invention relates to a new and distinct cultivar of Petunia plant, botanically known as *Petunia axillaris*, and hereinafter referred to by the cultivar name Michel.

The new cultivar is a product of a planned breeding program conducted by the inventor in Scharrachbergheim, France. The objective of the breeding program was to create new Petunia cultivars having desirable flower colors, small leaves, and strong healthy foliage and plants.

The new cultivar originated from a cross made by the inventor of the inventor's proprietary Petunia selection No. 94H, as the male or pollen parent, with the Petunia cultivar Surfinia Shihi Purple (not patented), as the female or seed parent, in June, 1993.

The cultivar Michel was discovered and selected by the inventor in November, 1993, as a flowering plant within the progeny of the stated cross in a controlled environment in Scharrachbergheim, France. Asexual reproduction of the new cultivar by terminal cuttings taken at Scharrachbergheim, France, has shown that the unique features of this new Petunia are stable and reproduced true to type in successive generations.

The cultivar Michel has not been observed under all possible environmental conditions. The phenotype may vary somewhat with variations in environment such as temperature and light intensity, without, however, any variance in genotype. The following observations, measurements and comparisons describe plants grown in Scharrachbergheim, France, under commercial production conditions.

The following traits have been repeatedly observed and are determined to be the unique characteristics of 'Michel'. These characteristics in combination distinguish 'Michel' as a new and distinct cultivar:

1. Bright red flowers that are slightly serrated.
2. Floriferous with numerous flowers per plant.
3. Early flowering.
4. Vigorous growth habit and moderate growth rate.
5. Spreading plant habit and very freely branching.
6. Strong, healthy foliage.
7. Moderately tolerant to rain, drought and temperature extremes.

The accompanying colored photographs illustrate the overall appearance of the new cultivar, showing the colors as true as it is reasonably possible to obtain in colored reproductions of this type.

The first photograph comprises a top perspective view of a typical hanging basket plant of the cultivar Michel.

The second photograph comprises a close-up view of individual flowers of the cultivar Michel. Flower and foliage colors in the photographs may appear different than the actual colors due to light reflectance.

In the following description, color references are made to The Royal Horticultural Society Colour Chart except where general terms of ordinary dictionary significance are used. Plants used for the description were grown in glass-covered greenhouses during the summer in Scharrachbergheim, France. Measurements are averages or ranges from ten specimens selected at random from five plants.

Botanical Classification: *Petunia axillaris* cultivar Michel.

Parentage:

*Male or pollen parent.*—Inventor's *Petunia axillaris* proprietary selection selection No. 94H.

*Female or seed parent.*—*Petunia axillaris* cultivar Surfinia Shihi Purple (not patented).

Propagation:

*Type cutting.*—Terminal vegetative cuttings.

*Time to initiate and develop roots.*—About ten days at 20C soil temperature.

*Rooting habit.*—Numerous, fine, fibrous, and well-branched.

Plant Description:

*Form.*—Indeterminate, decumbent, diffuse spreading, viscid, glandular pubescent.

*Branching habit.*—Very freely branching, usually about 8 branches per stem.

*Plant height (from soil level to top of plant plane).*—About 8 cm.

*Spreading area of plant.*—About 16 cm.

*Vigor.*—Vigorous, moderate growth rate.

*Crop time.*—10 to 12 weeks from a unrooted cutting to produce a finished and flowering 12.5-cm container.

*Foliage description.*—Leaves simple, generally symmetrical and long persisting. Leaves at first whorled, later alternate, somewhat fleshy. Size: Juvenile: Length: 3 to 4 cm. Width: 1.5 to 2 cm. Mature: Length: 6.5 to 7.5 cm. Width: 3.5 to 4.5 cm. Shape: Ovate. Apex: Acute. Base: Acute. Margin: Entire. Texture: Smooth. Color: Young foliage upper side: 137C. Young foliage under side: 137D. Mature foliage upper side: 137B. Mature foliage under side: 137C.

*Stem description.*—Diameter: 3 to 4 mm.

*Internode length.*—2 to 4 cm. Color: 137C. Texture: Very pubescent.

Flower Description:

*Flower type and habit.*—Large, single, salverform flowers, facing upwards, axillary. Calyx five-parted, petals united into a flower tube.

*Natural flowering season.*—Long day responsive, continuously flowers from spring through fall. Flowers self-cleaning.

*Quantity.*—Numerous flowers per plant.

*Flower bud.*—Length: 4.5 to 5 cm. Diameter: About 1 cm.

*Corolla.*—Diameter: 6.5 to 7.5 cm. Height: 5.5 to 6.5 cm. Petal quantity: Five, fused. Petal apex: Rounded. Margin: Entire, slightly serrated and undulating. Texture: Velvety, smooth and shiny. Color: Petal color, abaxial surface: 45D. Petal color, adaxial surface: 47D. Petal vein color, abaxial surface: 45B. Petal vein color, adaxial surface: 47C.

*Sepals.*—Quantity: Five. Shape: Linear to oblong. Apex: Obtuse to acute. Margin: Slightly lobed. Aspect: Upright. Color: Abaxial surface: 137C. Adaxial surface: 137D.

*Peduncle.*—Aspect: Erect. Size: Length: 2 to 3 cm. Width: About 1 mm. Color: 137D.)

*Reproductive organs.*—Stigma above anthers, superior ovary. Stamens: Stamen number: Five. Anther size: About 2 mm, generally larger than other varieties. Anther color: 14D. Pistils: Stigma color: 137A. Style length: About 2.3 cm.

Disease Resistance: Resistance to phytopathogens has not been noted under commercial conditions.

Seed production: Rarely observed.

It is claimed:

1. A new and distinct cultivar of Petunia plant named 'Michel', as illustrated and described.

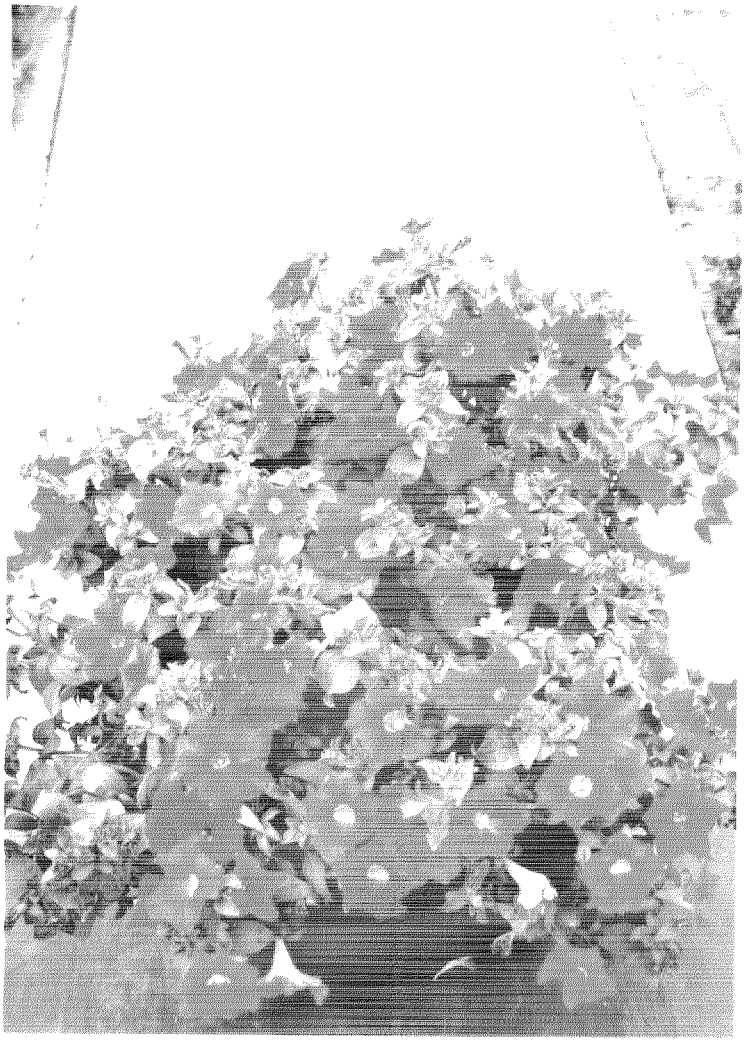

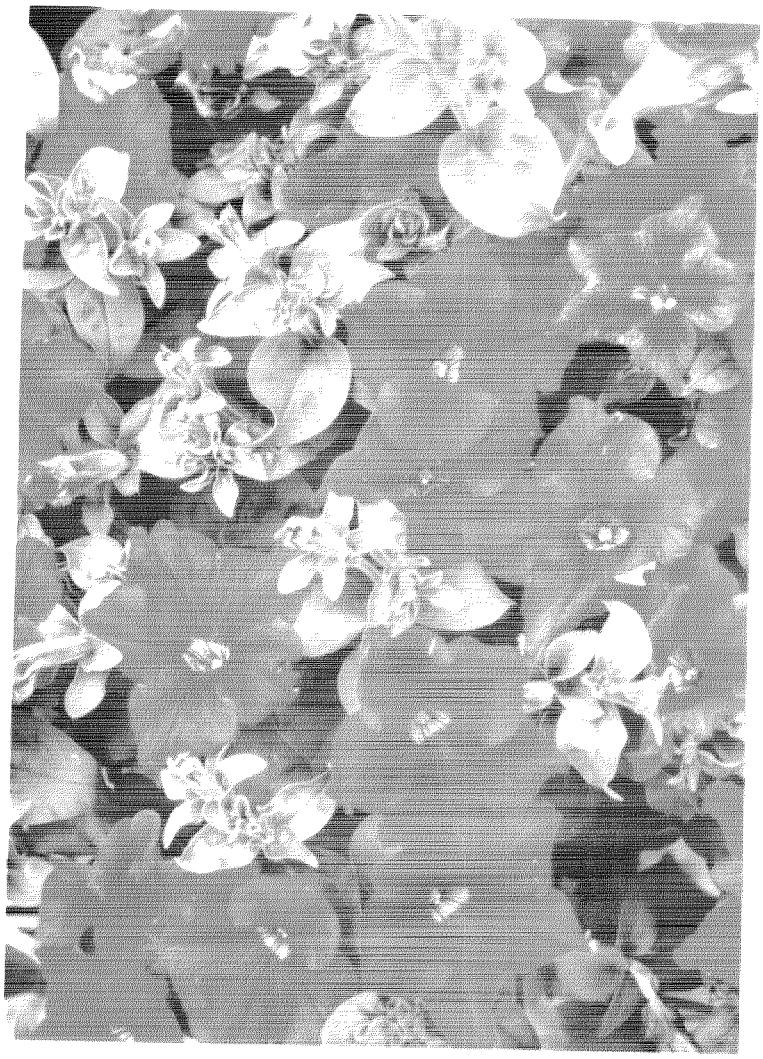

* * * * *